| United States Patent [19] | [11] Patent Number: 4,851,538 |
| Dudman | [45] Date of Patent: Jul. 25, 1989 |

[54] POLYAROMATIC COMPOUNDS

[75] Inventor: Christopher Dudman, Chester, England

[73] Assignee: Imperial Chemical Industries Plc, London, England

[21] Appl. No.: 870,863

[22] Filed: Jun. 5, 1986

[30] Foreign Application Priority Data

Jun. 14, 1985 [GB] United Kingdom ................ 8515063

[51] Int. Cl.$^4$ .......................................... C07D 213/22
[52] U.S. Cl. .................................................. 546/259
[58] Field of Search ................ 560/255, 140; 568/643, 568/633, 730, 719, 311, 315, 316, 32, 34; 546/259; 585/427; 562/469, 488, 427, 429

[56] References Cited

U.S. PATENT DOCUMENTS 3,979,459  9/1976  Rose ..................................... 568/333
4,276,226  6/1981  Clement et al. ................... 260/410.5

OTHER PUBLICATIONS

Chemical Abstracts, vol. 95, 1981, 115039y.
Synthesis, Jul. 1978, pp. 537–538.
Tetrahedron Letters, vol. 26, (1985), No. 13, pp. 1655–1658.
J.C.S. Perkin I, Reactions of Palladium(II) with Organic Compounds, Part III. Reactions of Aromatic Iodides in Basic Media, 1975, pp. 121–25.
JACS, 71(3), 1949, pp. 761, 776–779.

*Primary Examiner*—Werren B. Lone
*Attorney, Agent, or Firm*—Cushman, Darby & Cushman

[57] ABSTRACT

A halogen containing compound is coupled in the presence of carbon monoxide, an alkaline medium and a supported palladium catalyst. The reaction is preferably effected at elevated temperature and pressure, for example 80° C. to 200° C. and 0.2 to 3MNm$^{-2}$. The alkaline medium can be aqueous sodium hydroxide solution. The support of the supported palladium catalyst may be calcium carbonate or charcoal. The halogen containing aromatic compound can be, for example, chlorobenzene; 4-chlorotoluene; 4-methoxychlorobenzene; 4-chlorophenol; 4-chlorobenzoic acid; 4-chloro-4'-hydroxybenzophenone; 4-bromobenzoic acid; 4-bromophenol; 2-chlorotoluene; 2-hydroxy-5-chlorobenzoic acid or 2-chloropyridine. Some of the resulting compounds or derivatives thereof are novel, such as 4,4'-bis(4-acetoxybenzoyl) biphenyl, which is useful as an intermediate for preparing polyesters and polyethers.

12 Claims, No Drawings

POLYAROMATIC COMPOUNDS

The present invention relates to a process for the production of aromatic compounds containing at least two aromatic rings and to new aromatic compounds which can be obtained by the process.

Aromatic compounds containing more than one ring may be referred to as ring assemblies. Many compounds of this type are not readily available and have to be produced by condensation of aromatic compounds containing fewer rings, in particular derivatives of benzene. Ring assemblies containing substituent groups, for example —OH or —COOH groups are difficult to obtain and hence such compounds are expensive. Chemical Abstracts, Vol 95 (1981), abstract 115039y discloses the preparation of bisphenols by a coupling reaction of a halophenol in the presence of a palladium catalyst and a base. Using 4-chlorophenol a yield of about 30% of 4,4′-dihydroxybiphenyl was obtained. A coupling reaction using haloaryl compounds in the presence of sodium hydroxide, sodium formate, a surfactant and a palladium on charcoal is disclosed in Synthesis, July 1978, pages 537 and 538. Using the chloro compounds such as chlorobenzene, a yield of only about 50% of biphenyl is obtained in 24 hours. Furthermore, using this process we have found the reaction to be slow, in some instances giving conversions of about 20% after two hours, and we have been unable to prepare 4,4′-dihydroxybiphenyl.

Aromatic iodides couple in basic media in the presence of palladium (II) acetate but, under the same conditions, aryl bromides or chlorides do not appear to couple (J C S Perkin I, 1975 pages 121 to 125). Electroreductive coupling of aryl halides has been effected by elecrolysis in the presence of palladium catalysts (Tetrahedron Letters, vol 26, (1985), No 13, pages 1655 to 1658). However, whilst this process gives coupling using aryl iodides and aryl bromides, no coupling was achieved when corresponding aryl chloride was used. These latter two procedures require the use of aryl bromides or iodides rather than the more readily available chlorides. It is desirable to provide a process of preparing substituted ring assemblies which gives good yields in a relatively short time, preferably using readily available starting materials.

According to the present invention there is provided a process which comprises coupling a haloaromatic compound in the presence of carbon monoxide, an aqueous and/or alcoholic alkaline solution of an alkali metal or an alkaline earth metal hydroxide, carbonate or bicarbonate and a supported palladium catalyst wherein, under the reaction conditions, the haloaromatic compound, and the product of coupling, are each either a liquid and/or soluble in the reaction medium, and the haloaromatic compound has the general formula

where

Ar is a residue of an aromatic hydrocarbon compound or of a heterocyclic compound;

each R, which may be the same or different, is a hydrogen atom, a fluorine atom, a hydroxy group, a carboxylic acid group, an aliphatic hydrocarbon group, an aliphatic hydrocarbonoxy group, a group R′ CO— or a group R′ SR$_2$—;

R′ is a substituted or unsubstituted hydrocarbon group;

each X, which may be the same or different, is a halogen atom other than fluorine;

m is one or two; and n is equal to the residual valencies of the group Ar; with the proviso that the groups R on the ring atoms adjacent to the ring atom to which the group X is attached are other than hydroxy or carboxylic acid groups.

The group Ar may be a residue from benzene, biphenyl, a fused ring compound such as naphthalene or a heterocyclic compound such as pyridine. We prefer that the group Ar is monocyclic.

All of the groups R may be hydrogen atoms but we generally prefer that at least one of the groups R is other than hydrogen. If any groups R, which are other than hydrogen, are in the 2- or 6-position with respect to the group X, it is preferred that these groups are aliphatic hydrocarbon or aliphatic hydrocarbonoxy groups, particularly groups containing not more than 4 carbon atoms for example methyl or methoxy groups. We especially prefer that at least one of the groups R is, or contains, a hydroxy group or a carboxylic acid group. If one of the groups R is a group R′CO— or R′SO$_2$—, compounds of this type may be used to obtain ring assemblies which are useful as monomers for the preparation of polyaryletherketones or polyarylethersulphones, particularly when R′ is a hydroxysubstituted aromatic group such as a hydroxyphenyl group. Thus, the group R′ is preferably a substituted aromatic group, wherein the substituent group is a hydroxy group or a carboxylic acid group and, in particular, the group R′ is a hydroxysubstituted aromatic group.

The haloaromatic compound is preferably one having the general formula:

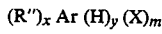

where

Ar, X and m are as defined;

each R″, which may be the same or different, is a fluorine atom, a hydroxy group, a carboxylic acid group, an aliphatic hydrocarbon group, an aliphatic hydroxycarbonoxy group, a group R′CO— or a group R′SO$_2$—;

R′ is as defined;

x is one or two; and y is equal to the residual valencies of the group Ar; with the proviso that any groups R″ on the ring atoms adjacent to the ring atom to which the group X is attached are aliphatic hydrocarbon or aliphatic hydrcarbonoxy groups.

The process of the present invention can be used for coupling haloaromatic compounds of the general formula:

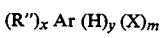

wherein

R″, Ar and X are as defines, x is one or two, m has a value of one and y has a value which is two or three less than the total valency of Ar. When x is one, then y has a value which is two less than the total valency of Ar, and the group Ar (H)$_y$ is a bivalent aromatic hydrocarbon group or a bivalent heterocyclic group, for example a phenylene group, preferably a para-phenylene group. The group X may be chlorine, bromine, or iodine. The chloro compounds are usually less costly than the corresponding bromo and iodo compounds. Furthermore, we have found that some carbonylation may occur during the coupling reaction and the extent of carbonylation is dependent on the nature of any groups R which are other than hydrogen, and also on the halogen atom. When one group R is a hydroxy group and the remaining groups R are hydrogen atoms, the lowest extent of carbonylation occures when X is a chlorine atom and hence it is preferred that X be a chlorine atom.

Compounds which may be used as the haloaromatic compounds include chlorobenzene; 4-chlorotoluene; 4-methoxychlorobenzene; 4-chlorophenol; 4-chlorobenzoic acid; 4-chloro-4'-hydroxybenzophenone; 4-bromobenzoic acid; 4-bromophenol; 4-iodophenol; 2-chlorotoluene; 3-chlorobenzoic acid; 2-hydroxy-5-chlorobenzoic acid and 2-chloropyridine.

The alkaline medium is an aqueous or alcoholic solution and may be a mixture of water and an alcohol. The alkaline medium preferably contains a stoichiometric quantity of base or a slight excess, for example of up to 10%. By "stiochiometric" in respect of the present process we mean two moles of a monoacid base (that is a base such as sodium hydroxide) for each group X present in the haloaromatic compound in addition to any base required to react with and other substituent groups which contain phenolic —OH or carboxylic acid groups. Hence for chlorobenzene or chlorotoluene the stiochiometric amount of base is 2 moles of monoacid base whilst for chlorophenol the stoichiometric amount of base is 3 moles of monoacid base and for chlorohydroxybenzoic acid the stiochiometric amount of base is 4 mole of monoacid base. The alkaline medium is a solution of an alkali metal or of an alkaline earth metal carbonate, bicarbonate, or hydroxide, for example sodium carbonate or sodium hydroxide.

The support of the supported palladium catalyst may be any suitable support and we have obtained satisfactory results when the support is calcium carbonate or carbon such as charcoal. In the supported catalyst, the proportion of the metal component is conveniently in the range 5 to 30% by weight, for example 10% by weight. The supported palladium catalyst is sensitive to impurities, particularly other metals, and the effect of the catalyst may be altered or destroyed by the presence of materials such as mercuric chloride or iron carbonyl. Hence, it is desirable to avoid the presence of other metals, apart from that present in the base.

The coupling reaction is preferably effected at elevated temperature and pressure. The temperature is preferably in the range 80° C. to 200° C., especially 100° C. to 150° C. The pressure is preferably in the range 0.2 to 3 $MNm^{-2}$, especially 0.05 to 2.0 $MNm^{-2}$. At lower temperatures and/or pressures the coupling reaction proceeds more slowly. At the preferred temperature and pressure the coupling reaction is essentially complete in about 3 hours. Depending on the particular monohaloaromatic compound used, a conversion of up to 95% and more may be achieved. The proportion of coupled product which is obtained may be as much as 100% of the product.

The haloaromatic compound and the product of the coupling reaction may be soluble in the reaction medium and if the reaction product is soluble it is then readily separated from the supported palladium catalyst by filtration or any other technique for separating liquid and solid. Accordingly, it is preferred that the reaction product is soluble in the reaction medium. The soluble product may then be recovered by acidification of the liquid and this usually results in precipitation of the free compound. This technique is applicable when the group R is, or contains, a hydroxy or carboxylic acid group. Alternatively, the reaction product can be obtained as an insoluble liquid which solidifies on cooling the reaction mixture. The reaction product is then obtained as an insoluble solid mixed with the heterogeneous catalyst and can then be recovered by dissolution in a suitable solvent, for example 4,4'-dimethoxybiphenyl may be extracted by dissolution in diethylether, the resulting solution being filtered from the solid catalyst and the 4,4'-dimethoxybiphenyl recovered by subsequent evaporation of the solvent. As a yet further alternative, the product of the coupling reaction may be converted to a more easily purified derivative, for example 4,4'-bis(4-hydroxybenzoyl) biphenyl may be treated with acetic anhydride to obtain the bis-acetate thereof which may be obtained in a satisfactory form by recrystallisation from chlorobenzene. If the haloaromatic compound is a liquid which is insoluble in the reaction medium, for example chlorobenzene or 4-chlorotoluene, we prefer to effect the coupling reaction in the presence of a phase transfer catalyst. Suitable phase transfer catalysts include quaternary ammonium salts containing at least one group containing at least 8 carbon atoms such as hexadecyl trimethylammonium bromide.

The process of the present invention is effected by contacting at least three phases (supported catalyst, alkaline medium and carbon monoxide) and hence it is desirable to ensure an adequate degree of mixing of the phases, for example to aid dissolution of the carbon monoxide in the liquid phase. Thus, it is desirable to effect the process under conditions of vigorous agitation.

Some of the haloaromatic compounds which can be used in the process of the present invention are of low solubility in the alkaline medium and when using such materials it is especially desirable to ensure a degree of agitation which is sufficient to give adequate mixing of the components.

The process of the present invention may be effecting using a haloaromatic compound which is a solid at ambient temperature but which is in the liquid phase under the reaction conditions either dissolved in the alkaline solution or as a molten material. Hence, if the haloaromatic compound is a solid and is of low solubility, or is essentially insoluble, in the alkaline medium, the process desirably is effected with vigorous agitation and at a temperature above that at which the haloaromatic compound becomes molten under the reaction conditions. Insoluble materials which remain solid under the reaction conditions appear to block the pores of the supported palladium catalyst and inhibit the reactions and hence such materials are not suitable for use in the process for the present invention.

If desired, a mixture of two or more haloaromatic compounds can be used in the process of the present invention. However, using such a mixture, a mixture of reaction products may be obtained and separation of the pure products may be difficult.

The process of the present invention is desirably effected in the absence of air. Any suitable process can be used to remove air from the reaction vessel before effecting the coupling reaction, for example by purging using an inert gas such as nitrogen or, very conveniently, using carbon monoxide, by evacuation of the reaction vessel followed by purging with an inert gas or carbon monoxide, or by pressurisation of the reaction vessel with an inert gas or carbon monoxide followed by venting to ambient pressure, this pressurisation and venting procedure being effected several times if desired.

The supported palladium catalyst may be recovered essentially unchanged from the product mixture. We have found that the catalyst can be reused with little if any treatment to separate the catalyst from the products of the previous process. It is generally preferred that the catalyst, before being reused, is treated to remove reactants and products from the previous reaction. Reactants and products may be removed from the catalyst by washing with a liquid medium, for example one which is solvent for the reactants and/or products. Two different solvents may be required, although a liquid medium which is a solvent for both the reactants and the products may be used, for example an aqueous alkaline solution for materials containing hydroxy or carboxylic acid groups. We have found that the heterogeneous catalyst can be reused and give satisfactory results after washing with water.

The supported palladium catalyst can be used in a small proportion relative to the haloaromatic compound which is to be coupled. Thus, the catalyst can be used in amounts of from 0.1% by weight of the catalytically active species relative to the amount of the haloaromatic compound. The catalytically active species is the palladium present in the supported palladium catalyst. It is preferred to avoid the use of large quantities of the supported catalyst and hence we prefer that the proportion of the catalytically active species does not exceed 5% by weight of the amount of the haloaromatic compound, and preferably does not exceed 2.5% by weight of the haloaromatic compound.

The coupling reaction may be effected for any suitable period of time and it should be appreciated that some coupling reaction proceed more rapidly than others. Generally the coupling reaction is essentially complete in 10 hours and many reactions are essentially complete in less than 5 hours, for example from 2 to 3 hours. In general a reaction time of at least 0.5 hours, and especially at least one hour, is desirable. However, using a larger proportion of catalyst, for example about 50% by weight, short reaction times of 10 to 15 minutes can be used.

The process of the present invention may be used to produce an extensive range of substituted and unsubstituted ring assemblies including some previously unknown compounds.

Thus, as a further aspect of the present invention there is provided, 4,4'-bis-(4-acetoxybenzoyl) biphenyl. This material has a melting point of 277° C.

The compounds obtained by the process of the present invention are ring assemblies and may be dihydroxy or bis carboxylic acid compounds. The dihydroxy and bis carboxylic acid compounds are useful materials for the preparation of polymeric materials by condensation with other compounds. In particular such materials may be used in the preparation of polyarylethers, including polyarylethersulphones and polyaryletherketones; polyesters; and polyamides using the known polymerisation techniques for the preparation of such polymers.

Various aspects of the present invention are set out in the following examples which are illustrative of the invention.

EXAMPLE 1

4-methoxychlorobenzene (3 g), sodium hydroxide (3 g), water (25 cm$^3$) and 10%-palladium or carbon catalyst (0.5 g) were added to a 100 cm$^3$ glass liner contained in a stainless steel autoclave of capacity 200 cm$^3$. The autoclave was pressurised with carbon monoxide to a pressure of 1.7 MNm$^{-2}$ and was then vented to ambient pressure (about 0.1 MNm$^{-2}$). This procedure was carried out three times. The autoclave was finally pressurised with carbon monoxide to a pressure of 1.7 MNm$^{-2}$. The contents of the autoclave were stirred and heated up to 120° C. After 3 hours at 120° C., the mixture was cooled, the vessel vented to ambient pressure and the solution acidified with Molar aqueous hydrochloric acid. The produce was precipitated, to give a solid mixture of the product with the catalyst. This solid was filtered off and washed with water (200 cm$^3$). The solid product was extracted by stirring with diethyl ethyer (100 cm$^3$) at ambient temperature until solution was obtained. The solution obtained was filtered to remove the catalyst and the solvent was removed from the filtrate by evaporation at ambient temperature and under reduced pressure (2 kNm$^{-2}$) to give 4,4'-dimethoxybiphenyl. Analysis of the product by gas chromatography indicated a yield of 84% by weight relative to the 4-methoxychlorobenzene.

COMPARATIVE EXAMPLE A

In this comparative example, a procedure similar to that described in Synthesis, July 1978, pages 537 and 538 was used to effect the coupling of 4-methoxychlorobenzene.

4-methoxychlorobenzene (7.125 g, 0.5 moles) was added to a solution of sodium hydroxide (32 g, 0.8 moles), sodium formate (3.4 g, 0.05 moles), and benzyl trimethyl ammonium chloride (surfactant, 2 g) in water (100 cm$^3$). 10% Palladium on charcoal (0.5 g) was then added and the mixture was refluxed under nitrogen with vigorous stirring for two hours. After that time, the mixture was cooled and the catalyst removed by filtration. The organic material was then extracted by shaking the solution, in a separating funnel, with three 30 cm$^3$ portions of diethyl ether. Gas chromatography showed the reaction to have proceed to about 20% conversion of the 4-methoxychlorophenol, and the product comprised 40% by weight of 4,4'-dimethoxybiphenyl and 60% by weight of anisole.

EXAMPLE 2

A solution of 4-chlorobenzoic acid (3.15 g) and sodium hydroxide (4.06 g) in water (45 cm$^3$) was prepared in the glass liner and stainless steel autoclave of Example 1. 10%-palladium on charcoal catalyst (0.2 g) was added. The autoclave was pressurised with carbon monoxide and vented as in Example 1, and finally pressurised to 1.7 MN m$^{-2}$ with carbon monoxide. The contents of the autoclave were stirred and heated to 150° C. After 2.5 hours at 150° C. the autoclave was cooled to room temperature and vented. The catalyst was filtered off and the solution acidified with molar aqueous hydrochloric acid. The precipitate was filtered off, then benzoic acid was removed by extraction with boiling water (200 cm$^3$), from which the benzoic acid separated on cooling. An extraction with boiling ethanol (200 cm$^3$) was performed to extract any unreacted 4-chlorobenzoic acid, but none was isolated. The solid was then dried to give 1.25 g (about 50% yield) of 4,4'-biphenyldicarboxylic acid, which was pure by proton nmr. The only other product obtained was benzoic acid, identified by melting point and infra-red spectrum.

EXAMPLE 3

4-chlorophenol (2.5 g, 19.5 mmol) was dissolved in a solution of sodium hydroxide (3 g, 75 mmol) in water (25 cm$^3$) in the liner and autoclave described in Example 1. 10% palladium on charcoal (0.5 g) was added. The autoclave was pressurised to 0.86 MNm$^{-2}$ with carbon monoxide and vented, this being effected three times as in Example 1. The autoclave was then pressurised to 0.86 MNm$^{-2}$ with carbon monoxide. The contents of the autoclave were vigorously stirred with a magnetic stirrer and heated to 106° C. The mixture was maintained at 106° C., with stirring, for three hours and was then cooled. The autoclave was flushed with nitrogen, then the catalyst was removed by filtration and the filtrate acidified with aqueous Molar sulphuric acid. The precipitate was extracted by shaking in a separating funnel with three 50 cm$^3$ portions of diethyl ether. The ethereal solution was analysed by GLC, using resorcinol as an added standard. The products obtained were phenol (43% by weight yield) and 4,4'-dihydroxybiphenyl (57% by weight yield). A conversion of 92% was achieved.

COMPARATIVE EXAMPLE B

In this comparative example, the procedure of Synthesis, July 1978, pages 537 and 538 was used in an attempt to effect coupling of 4-chlorophenol.

4 Chlorophenol (25.7 g, 0.2 moles) was dissolved in a solution of sodium hydroxide (40 g, 1 mole) in water (110 cm$^3$) then sodium formate (15.0 g, 0.22 moles) and 10% palladium on charcoal were added. The mixture was heated to reflux under nitrogen with stirring for two hours, then cooled and filtered to remove the catalyst. The mixture was acidified with 10M hydrochloric acid. The organic material was extracted into diethyl ether. Gas chromatograph showed only phenol to be present.

EXAMPLE 4

4-chloro-4'-hydroxybenzophenone (4.64 g, 20 mmol) was added to a solution of sodium hydroxide (4 g, 0.1 mol) in water (45 cm$^3$) in the liner and autoclave described in Example 1. 10% palladium on charcoal (0.12 g) was added. The autoclave was pressurised with carbon monoxide ad vented as in Example 1 with the exception that the pressure was 0.7 MNm$^{-2}$. The autoclave was then pressurised to 0.7 MNm$^{-2}$ with carbon monoxide. The contents of the autoclave were vigorously stirred with a magnetic stirrer and heated to 106° C. The mixture was maintained at 106° C., with stirring, for four hours.

After that time, the mixture was cooled and the vessel flushed with nitrogen. The catalyst was removed by filtration and the filtrate acidified with aqueous Molar hydrochloric acid. The precipitate was collected by filtration, washed with water and drained well. The product was dissolved in 50 cm$^3$ of acetone and the mixture was filtered to remove sodium chloride. The filtrate was evaporated, the solid obtained (4 g) was refluxed in acetic anhydride (50 cm$^3$) for 30 minutes and the mixture allowed to cool. The product was collected by filtration, and dried. The yield of 4,4'-bis (4-acetoxybenzoyl) biphenyl was 3.6 g, 70%. The bis-acetate was identified by IR, NMR and mass spectroscopy (M$^+$ 478) and was found to have a melting point of 277° C.

The filtrate obtained from the treatment with acetic anhydride was added to water and a yellow solid was precipitated. This solid was isolated and found to be acetylated starting material, yield 1.36 g, 29%. No hydrogenated product (that is 4-hydroxybenzophenone) was detected.

EXAMPLE 5

The palladium-on-charcoal catalyst used in the chlorobenzoic acid coupling process of Example 2 was recovered by filtration and used to repeat the chlorophenol coupling of Example 3. Under these conditions a conversion of 65% was achieved. The products obtained were phenol (62% by weight yield) and 4,4'-dihydroxybiphenyl (38% by weight yield).

EXAMPLE 6

About two thirds of the catalyst used in Example 3 was recovered, washed with water and used directly in an exactly similar reaction mixture under the same conditions. Gas chromatography showed the reaction to have proceeded to 75% conversion, the product mixture comprising 53% 4,4'-dihydroxybiphenyl and 47% phenol, by weight.

EXAMPLE 7

Sodium hydroxide (120 g, 3 moles) was dissolved in water (1.2 dm$^3$) and 3-chlorobenzoic acid (120 g, 0.77 moles) was added, followed by 10% palladium on charcoal (20 g, 2 mmol of Pd). The mixture was placed in 2 cm$^3$ glass liner in an autoclave. The autoclave was flushed thoroughly with carbon monoxide, and was then pressurised with carbon monoxide to a pressure of 2 MNm$^{-2}$. The mixture was mechanically stirred and heated to 150° C. After two hours the absorption of carbon monoxide had ceased, so the mixture was cooled and the autoclave was vented. The cold suspension was filtered, and the precipitate (which comprised the disodium salt of the coupled product mixed with the catalyst) was extracted with boiling water (1 dm$^3$) and filtered hot. The filtrate was cooled and carefully acidified with concentrated hydrochloric acid to a pH of 5.7. The monosodium salt of the diacid was filtered off and washed with cold water (200 cm$^3$) then stirred in 1M of hydrochloric acid (1 dm$^3$) for one hour. The diacid was then filtered off and washed with cold water 1 dm$^3$) then dried at 120° C. and at 2.5 kNm$^{-2}$. A yield of 79 g (85%).

COMPARATIVE EXAMPLE C 3-chlorobenzoic acid (3 g, 20 mmol) was dissolved in 30 cm$^3$ of a stock solution of sodium hydroxide in water (10% w/v : 75 mmol). Sodium formate (2 g, 28 mmol) and 10% palladium on charcoal (0.5 g) were added. The mixture was placed in a 150 cm$^3$ glass liner in an autoclave, and was heated to 120° C. under nitrogen for two hours. The mixture was allowed to cool, then was filtered to remove the catalyst, there was no other precipitate. The filtration was acidified with 1M hydrochloric acid to pH 1, and the precipitate was filtered off. The precipitate was identified as benzoic acid. Yield 2.2 g (80%).

COMPARATIVE EXAMPLES D TO F

The procedure of Example 1 was repeated replacing 4-methoxychlorobenzene with 2-chlorobenzoic acid, 4-fluorobenzoic acid and 4-fluorophenol respectively. These materials were found to be completely unreactive, the starting material being removed quantitatively in all cases.

COMPARATIVE EXAMPLE G 2-bromobenzoic acid (3 g, 15 mmol) was dissolved in 20 cm$^3$ of a stock solution of sodium hydroxide (10% w/v, 50 mmol). Palladium on charcoal (10%, 0.5 g) was added, and the mixture was placed in a 150 cm$^3$ glass liner in an autoclave. The autoclave was thoroughly flushed with carbon monoxide, then was pressurised with carbon monoxide to 2 MNm$^{-2}$ and heated to 150° C. After three hours the mixture was allowed to cool, the autoclave was vented, and the catalyst was filtered off; no other precipitate was present. The filtrate was acidified with 1M hydrochloric acid to pH1, then the precipitate was filtered off and identified as benzoic acid, which was obtained in a yield of 1.6 g, (90%).

COMPARATIVE EXAMPLE H 2-chlorophenol (2.5 g, 20 mmol) was dissolved in 25 cm$^3$ of a stock solution of sodium hydroxide (10% w/v, 62 mmol). Palladium on charcoal (10%, 0.5 g) was added. The mixture was placed in a 150 cm$^3$ glass liner in an autoclave. The autoclave was flushed with carbon monoxide, then pressurised with carbon monoxide to 2 MNm$^{-2}$ and heated to 120° C.

After three hours, the mixture was allowed to cool, and the catalyst was removed by filtration. The filtrate was acidified with 1M hydrochloric acid, and the aqueous solution was extracted with three 20 cm$^3$ portions of diethyl ether. GLC analysis of the ethereal solution showed that 50% of the 2-chlorophenol was reacted, and had been converted solely to phenol.

EXAMPLE 8

4-chlorotoluene (2.5 g, 20 mmol) was added to 25 cm$^3$ of a solution of sodium hydroxide in water (10% w/v) containing palladium on charcoal in suspension (10%, 0.5 g). The mixture was placed in a 150 cm$^3$ glass liner in an autoclave, and the autoclave was thoroughly flushed with carbon monoxide. The autoclave was pressurised with carbon monoxide to 2 MNm$^{-2}$, and heated to 120° C. with vigorous stirring. After three hours, the mixture was allowed to cool and the catalyst was removed by filtration. The aqueous filtrate was extracted with three 20 cm$^3$ portions of diethyl ether, and the organic extractants were analysed by gas chromatography. The reaction had proceeded to 71% conversion. 42 mol % of the product was 4,4'-dimethylbiphenyl, 56 mol % was toluene, and 2 mole % was 4-methylbenzoic acid.

EXAMPLE 9

4-chlorotoluene (2.5 g, 20 mmol) was added to 25 cm$^3$ of a solution of sodium hydroxide (10% w/v) containing hexadecyl trimethylammonium bromide (1 g, 4 mmol) and palladium on charcoal (10%, 0.5 g). The mixture was placed in a glass liner in an autoclave, which was flushed thoroughly with carbon monoxide, then pressureised to 2 MNm$^{-2}$. The mixture was heated to 120° C. with vigorous stirring for three hours, then allowed to cool. The catalyst was removed by filtration and the aqueous solution was extracted with three 20 cm$^3$ portions of diethyl ether. The organic extracts were analysed by gas chromatography, which showed the reaction had proceeded to 80% conversion, and 77 mol % of the product was 4,4'-dimethylbiphenyl, the remainder being toluene.

EXAMPLE 10

The procedure of Example 9 was repeated using 2-chlorotoluene to give a 60% overall yield of 2,2'-dimethylbiphenyl.

EXAMPLE 11

2-hydroxy 5-chlorobenzoic acid (3.4 g, 20 mmol) was dissolved in 45 cm$^3$ of a sodium hydroxide solution (10% w/v) and palladium on charcoal (10%, 0.5 g) was added. The mixture was placed in a glass liner in an autoclave which was flushed thoroughly with carbon monoxide, then pressurised with carbon monoxide to 2 MNm$^{-2}$ and heated to 120° C. with stirring for three hours. The mixture was then allowed to cool, the catalyst removed by filtration, and the product precipitated from the aqueous solution by acidification to pH1 with 1M hydrochloric acid. The coupled product (4,4'-dihydroxybiphenyl 3,3'-dicarboxylic acid) was obtained in 80% yield.

EXAMPLE 12

4-chlorophenol (2.5 g, 20 mmol) was dissolved in 25 cm$^3$ of a stock solution of sodium hydroxide (10% w/v, 62 mmol). Palladium on calcium carbonate (5%, 0.5 g) was added. The mixture was placed in a 150 cm$^3$ glass liner in an autoclave. The autoclave was flushed with carbon monoxide to 2 MNm$^{-2}$ and heated to 120° C.

After three hours, the mixture was allowed to cool, and the catalyst was removed by filtration. The filtrate was acidified with 1M hydrochloric acid, and the aqueous solution was extracted with three 20 cm$^3$ portions of diethyl ether. GLC analysis of the ethereal solution showed that 90% of the 4-chlorophenol had reacted, and the product mixture comprised 60 mol % coupled product, 15 mol % carbonylated product, and 25 mol % dehalogenated product.

EXAMPLE 13

4-bromobenzoic acid (8.02 g, 40 mmol) was dissolved in 55 cm$^3$ of a stock solution of sodium hydroxide (10%, 140 mmol). Palladium on charcoal (10%, 0.5 g) was added, and the mixture was placed in a 150 cm$^3$ glass liner in an autoclave. The autoclave was thoroughly flushed with carbon monoxide, then was pressurised with carbon monoxide, to 2 MNm$^{-2}$ and heated to 150° C. After three hours the mixture was allowed to cool, the autoclave was vented, and the mixture filtered. The precipitate, which comprised the catalyst mixed with the disodium salt of the diacid, was extracted with 100 cm$^3$ of boiling water and the hot suspension was filtered. After it had cooled, the filtrate was acidified with 1M hydrochloric acid to pH1 and the product was recovered by filtration. The product was biphenyl 4,4' dicarboxylic acid in a yield of 3.3 g (70%).

EXAMPLE 14

4-bromophenol (3.5 g, 20 mmol) was dissolved in 27 cm$^3$ of a stock solution of sodium hydroxide (10% w/v, 68 mmol). Palladium on charcoal (10%, 0.5 g) was added. The mixture was placed in a 150 cm$^3$ glass liner in an autoclave. The autoclave was flushed with carbon monoxide, then pressurised with carbon monoxide to 2 MNm$^{-2}$ and heated to 120° C.

After three hours, the mixture was allowed to cool, and the catalyst was removed by filtration. The filtrate was acidified with 1M hydrochloric acid, and the aqueous solution was extracted with three 20 cm³ portions of diethyl ether. GLC analysis of the ethereal solution showed that all of the 4-bromophenol had reacted, and the product mixture comprised 4-hydroxybenzoic acid (17 mol %), phenol (24 mol %), and 4,4' dihydroxybiphenyl (59 mol %).

EXAMPLE 15

4-bromobipheny (4.7 g, 20 mmol) was added to 27 cm³ of a stock solution of sodium hydroxide (10% w/v, 68 mmol). Palladium on charcoal (10%, 0.5 g) and hexadecyl trimethyl ammonium bromide (1 g) were added. The mixture was placed in a 150 cm³ glass liner in an autoclave. The autoclave was flushed with carbon monoxide, then pressurised with carbon monoxide to 2 MNm$^{-2}$ and heated to 150° C. with vigorous stirring. After three hours, the mixture was allowed to cool, and the catalyst was removed by filtration. The filtrate was extracted with three 20 cm³ portions of diethyl ether. GLC analysis of the ethereal extracts showed the reaction to have proceeded to 10% conversion, the sole product being quaterphenyl.

EXAMPLE 16

2-bromotoluene (3.4 g, 20 mmol) was added to 27 cm³ of a stock solution of sodium hydroxide (10% w/v, 68 mmol). Palladium on charcoal (10%, 0.5 g) and hexadecyl trimethyl ammonium bromide (1 g) were added. The mixture was placed in a 150 cm³ glass liner in an autoclave. The autoclave was flushed with carbon monoxide, then pressurised with carbon monoxide to 2 MNm$^{-2}$ and heated to 150° C. with vigorous stirring. After three hours, the mixture was allowed to cool, and the catalyst was removed by filtration. The filtrate was extracted with three 20 cm³ portions of diethyl ether. GLC analysis of the ethereal extracts showed the reaction products to comprise 55 mol % 2,2'-dimethylbiphenyl, 40 mol % toluene, and 5 mol % 2-methylbenzoic acid.

EXAMPLE 17

2-bromoanisole (3.74 g, 20 mmol) as added to 27 cm³ of a stock solution of sodium hydroxide (10% w/v, 68 mmol). Palladium on charcoal (10%, 0.5 g) and hexadecyl trimethyl ammonium bromide (1 g) were added. The mixture was placed in a 150 cm³ glass liner in an autoclave. The autoclave was flushed with carbon monoxide, then pressurised with carbon monoxide to 2 MNm$^{-2}$ and heated to 150° C. with vigorous stirring. After three hours, the mixture was allowed to cool, and the catalyst was removed by filtration. The filtrate was extracted with three 20 cm³ portions of diethyl ether. GLC analysis of the ethereal extracts showed the reaction products to comprise 45 mol % 2,2'-dimethyoxybiphenyl, 40 mol % anisole, and 5 mol % 2-, methylbenzoic acid.

EXAMPLE 18

4-iodophenol (4.4 g, 20 mmol) was dissolved in 27 cm³ of a stock solution of sodium hydroxide (10% w/v, 68 mmol). Palladium on charcoal (10%, 0.5 g) was added. The mixture was placed in a 150 cm³ glass liner in an autoclave. The autoclave was flushed with carbon monoxide to 2 MNm$^{-2}$ and heated to 120° C.

After three hours, the mixture was allowed to cool, and the catalyst was removed by filtration. The filtrate was acidified with 1M hydrochloric acid, and the aqueous solution was extracted with three 20 cm³ portions of diethyl ether. GLC analysis of the ethereal solution showed that all of the 4-iodophenol had reacted, and the product mixture comprised 4-hydroxybenzoic acid (51 mol %), phenol (28 mol %) and 4,4'-dihydroxybiphenyl (4 mol %).

EXAMPLE 19

2-chloropyridine (2.5 g, 20 mmol) was dissolved in 25 cm³ of a stock solution of sodium hydroxide (10% w/v, 62 mmol). Palladium on charcoal (10%, 0.5 g) was added. The mixture was placed in a 150 cm³ glass liner in an autoclave. The autoclave was flushed with carbon monoxide, then pressurised with carbon monoxide to 2 MNm$^{-2}$ and heated to 120° C.

After three hours, the mixture was allowed to cool, and the catalyst was removed by filtration. The filtrate was acidified with 1M hydrochloric acid, and the aqueous solution was extracted with three 20 cm³ portions of diethyl ether. GLC analysis of the ethereal solution showed that 95% of the 2-chloropyridine had reacted, and that the product mixture comprised 95 mol % 2,2'bipyridyl and 5 mol % pyridine.

EXAMPLE 20

4-chlorophenol (4.4 g, 20 mmol) was dissolved in water (25 cm³) and calcium hydroxide (2.2, 30 mmol) was added, followed by palladium on charcoal (10%, 0.5 g). The mixture was placed in a 150 cm³ glass liner in an autoclave. The autoclave was flushed with carbon monoxide, then pressurised with carbon monoxide to 2 MNm$^{-2}$ and and heated to 120° C. After three hours, the mixture was allowed to cool, and the catalyst was removed by filtration. The filtrate was acidified with 1M hydrochloric acid, and the aqueous solution was extracted with three 20 cm³ portions of diethyl ether. GLC analysis of the ethereal solution showed that 30% of the 4-chlorophenol had reacted, and that 33 mol % of the product was coupled product, and 64 mol % was phenol.

EXAMPLE 21

4-chlorophenol (4.4 g, 20 mmol) was dissolved in water (25 cm³) and sodium carbonate (3.2 g, 30 mmol) was added, followed by palladium on charcoal (10%, 0.5 g). The mixture was placed in a 150 cm³ glass liner in an autoclave. The autoclave was flushed with carbon monoxide, then pressurised with carbon monoxide to 2 MNm$^{-2}$ and heated to 120° C. After three hours, the mixture was allowed to cool, and the catalyst was removed by filtration. The filtrate was acidified with 1M hydrochloric acid, and the aqueous solution was extracted with three 20 cm³ portions of diethyl ether. GLC analysis of the ethereal solution showed that 50% of the 4-chlorophenol had reacted, and that 30 mol % of the product was the coupled product, and 70 mol % was phenol.

I claim:

1. A process comprising coupling a haloaromatic compound in the presence of carbon monoxide, and aqueous and/or alcoholic alkaline solution of an alkali metal or an alkaline earth metal hydroxide, carbonate or bicarbonate and a supported palladium catalyst wherein, under the reaction conditions, the haloaromatic compound, and the product of coupling, are each either a liquid and/or soluble in the reaction medium, and the haloaromatic compound has the general formula $(R)_n Ar(X)_m$ where Ar is a residue of an aromatic hydrocarbon compound, pyridine, or chloropyridine;

each R, which may be the same or different, is a hydrogen atom, a fluorine atom, a hydroxy group, a carboxylic acid group, an aliphatic hydrocarbon group, an aliphatic hydrocarbonoxy group, a group R'CO— or a group R'SO$_2$—;

R' is a hydrocarbon group which is unsubstituted or carries a substituent selected from the class consisting of hydroxyl and carboxy and;

each X, which may be the same or different, is a halogen atom other than fluorine;

m is one or two; and n is equal to the residual valencies of the group Ar, with the proviso that the groups R on the ring atoms adjacent to the ring atom to which the group X is attached are other than hydroxy or carboxylic acid groups.

2. The process of claim 1 wherein the group Ar is a residue from benzene, biphenyl or pyridine.

3. The process of claim 1 wherein at least one of the groups R is, or contains, a hydroxy group or a carboxylic acid group.

4. The process of claim 3 wherein at least one of the groups R is R'CO— or R'SO$_2$— and R' is a hydroxysubstituted aromatic group.

5. The process of claim 1 wherein X is chlorine.

6. The process of claim 1 wherein the haloaromatic compound is at least one of chlorobenzene; 4-chlorotoluene; 4-methoxychlorobenzene; 4-chlorophenol; 4-chlorobenzoic acid; 4-chloro- 4'-hydroxybenzophenone; 4-bromobenzoic acid; 4-bromophenol; 4-bromobiphenyl; 4-iodophenol; 2-chlorotoluene; 2-bromotoluene; 2-methoxybromobenzene; 3-chlorobenzoic acid; 2-chloropyridine and 2-hydroxy-5-chlorobenzoic acid.

7. The process of claim 1 wherein the alkaline medium contains a stiochiometric quantity, or an excess of up to 10%, of a base, where stoichiometric means the equivalent to two moles of a monoacid base for each group X which is present in the haloaromatic compound in addition to any base which is required to react with groups which contain phenolic —OH or carboxylic acid groups and which are present in the haloaromatic compound.

8. The process of claim 1 wherein the solution is an aqueous solution of an alkali metal hydroxide.

9. The process of claim 1 wherein the catalyst is palladium on calcium carbonate or carbon.

10. The process of claim 1 which is effected at a temperature in the range 80° C. to 200° C.

11. The process of claim 1 which is effected at a pressure in the range 0.2 to 3 MNm$^{-2}$.

12. The process claim 1 wherein the reaction product is a dihydroxy material and is treated with acetic anhydride to obtain the corresponding bis-acetate.

* * * * *